_United States Patent_ [19]

Frangioni

[11] Patent Number: 5,069,773
[45] Date of Patent: Dec. 3, 1991

[54] ELECTROPHORETIC GEL FORMING SYSTEM

[76] Inventor: John V. Frangioni, 128 Rawson Rd., Arlington, Mass. 02174

[21] Appl. No.: 651,204

[22] Filed: Feb. 6, 1991

[51] Int. Cl.⁵ .................. B01D 61/42; C25D 13/00
[52] U.S. Cl. ...................... 204/299 R; 204/182.8; 206/219
[58] Field of Search .............. 204/299 R, 182.8; 525/288; 430/208; 206/219, 618, 632, 601

[56] References Cited
U.S. PATENT DOCUMENTS 4,188,219 2/1980 Cawley .................. 430/208
4,810,456 3/1989 Bence, III et al. ........... 204/182.8
4,864,003 9/1989 Fujimoto et la. ............ 525/288

_Primary Examiner_—John Niebling
_Assistant Examiner_—Caroline Koestner
_Attorney, Agent, or Firm_—Lyon & Lyon

[57] ABSTRACT

Apparatus and method for forming an electrophoretic gel having a polymer. The apparatus has at least two sealed compartments, with separate inner volumes. The inner volumes are separated from each other by at least one burstable seal. In one inner volume is a monomer which can be polymerized to form the polymer. In other inner volume is a catalyst. Bursting of the burstable seal allows the monomer and catalyst to contact each other and, in conjuction with any other necessary components held within the apparatus, to form a liquid medium in the apparatus which will then form the electrophoretic gel under suitable conditions.

23 Claims, 1 Drawing Sheet

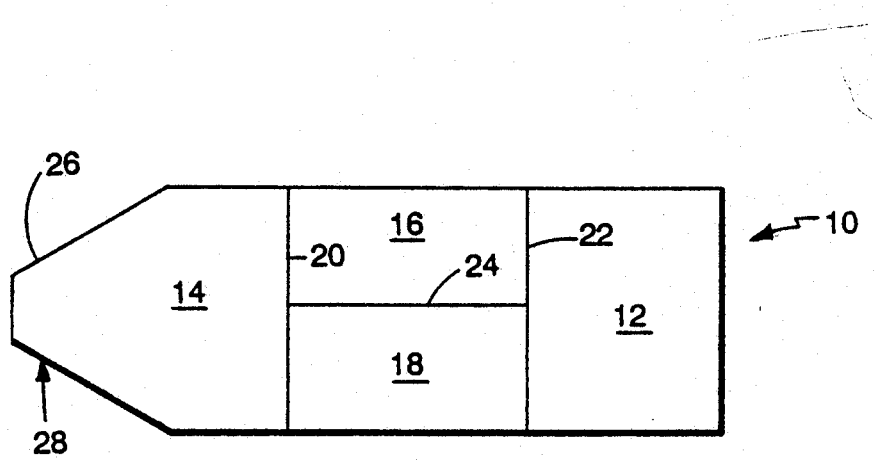
FIGURE

ELECTROPHORETIC GEL FORMING SYSTEM

BACKGROUND OF THE INVENTION

This invention relates to methods and apparatus for producing electrophoretic gels which require polymerization of material during their formation.

The analysis of complex biochemical systems is dependent on technology which allows individual molecules to be separated. Standard techniques exist which allow protein, DNA, and RNA molecules to be separated and/or purified on the basis of their size, electrical charge, physical structure or a combination thereof. Most of these techniques employ at least one type of gel electrophoresis. In gel electrophoresis, the molecules to be separated are subjected to an electric field which causes them to enter a gel of a known pore size, charge and pH. Depending on the conditions, different molecules will be either retarded or accelerated as they pass through the gel, and hence separated.

One of the most common materials used for electrophoresis is polyacrylamide. A polyacrylamide gel is formed by the chemical cross-linking of a monomer, acrylamide, with a co-monomer, such as N,N'-methylenebisacrylamide (BIS), N,N'-bisacrylylcystamine (BAC), N,N'-(1,2-dihydroxyethylene) bisacrylamide (DHEBA), or N,N'-diallyltartardiamide (DATD). The ratio, as well as the concentration of these monomers determines the final pore size, and hence sieving properties of the gel. Chemical cross-linking, or polymerization, of the gel is effected by the formation of free radicals by an initiator, such as ammonium persulfate (APS) or riboflavin. Polymerization is made even more efficient by the addition of an accelerator such as N,N,N',N'-tetramethylethylenediamine (TEMED) or 3-dimethylaminoproprionitrile (DMAPN).

Non-acrylamide chemically cross-linked matrices have recently come to market. See e.g., AT Biochem, Inc. catalog. These are prepared in a manner similar to polyacrylamide gels.

Generally, an electrophoretic gel is prepared in the following manner. While wearing gloves, and typically in a fume hood, the user prepares the monomer and co-monomer as concentrated aqueous stock solutions which are stored at 4° C. until use. An initiator such as APS is prepared on the day of use as an aqueous solution and stored at 4° C. Accelerators such as TEMED are provided as liquids. Other components of the gel depend on the type of molecules to be separated. For example, for one-dimensional separation of proteins, water, Tris(hydroxymethyl)methylamine (TRIS) and sodium dodecyl sulfate (SDS) are usually prepared as aqueous stock solutions. These four stock solutions are then mixed to prepare a final liquid which is then poured into a suitable apparatus and allowed to polymerize to form a polyacrylamide gel.

SUMMARY OF THE INVENTION

The present invention concerns an apparatus and method for overcoming a long standing problem in the gel forming field. Acrylamide is a potent neurotoxin, and chronic exposure to this chemical in either solid or liquid form results in a well recognized clinical condition characterized by a large fiber neuropathy and sensory ataxia. Other chemicals used to form polyacrylamide gels, such as BIS, APS, BAC, DMAPN and TEMED, are either known toxins or have undetermined safety risks. The present invention allows a gel to be formed without need for pipetting or handling of toxic solutions, while maintaining flexibility in the structure of the final polymerized gel. Moreover, the apparatus so described has a long potential shelf-life, and can be adapted for use in separation of proteins, DNA, and RNA.

The distinct advantages of this system over conventional methods are as follows: the apparatus and method of its use minimizes contact with acrylamide, or its equivalent, and other known toxins; allows gel preparation to be accomplished by a complete novice in very little time; minimizes time required for gel preparation by eliminating the need to prepare at least four different stock solutions; potentially increases reproducibility of gel preparation; has a long potential shelf life; and is good for the environment since extensive disposable plasticware and washable glassware are no longer required to prepare the resulting polyacrylamide gel.

Thus, in a first aspect, the invention features an apparatus for forming an electrophoretic gel which includes a polymer, e.g., polyacrylamide. The apparatus has at least two sealed compartments with inner volumes separated from each other by at least one burstable seal. One inner volume contains a monomer which can be polymerized to form the polymer, the other inner volume includes a catalyst, such as an accelerator or initiator. Bursting of the burstable seal allows the monomer and catalyst to contact each other and, in conjunction with any other necessary components held within the apparatus, to form a liquid medium in the apparatus suitable for forming the desired gel.

The burstable seal is chosen from one of many well known in the art such that it is broken, and the relevant components mixed, only when suitable external pressure is applied. The whole apparatus, of course, includes an outer layer of non-burstable material which encloses all the necessary chemical components. By monomer is meant to include chemicals such as acrylamide which copolymerize with other monomers, e.g., BIS, to form the final polymeric gel. By catalyst is meant to include accelerators and initiators alone and in combination.

In a related aspect, the invention features an apparatus with at least two sealed compartments, each having separate inner volumes. The apparatus includes all of the chemical components necessary to form the electrophoretic gel. One or more of those components is provided in one inner volume and one or more of the components is provided in the other inner volume. The inner volumes are separated from each other by at least one burstable seal. Bursting of the burstable seal allows contact of the two inner volumes and thereby contact of the components held within those inner volumes. When all the components are contacted within the apparatus a liquid medium for forming the electrophoretic gel is provided.

In yet another related aspect, the invention features apparatus with four compartments separated by burstable seals. In each compartment is a monomer, initiator, accelerator or liquid buffer. The seals can be broken to allow mixing of the contents of each compartment, and thereby production of the desired liquid medium to form a polymeric gel.

In preferred embodiments, the apparatus includes a co-monomer which co-polymerizes with the monomer to form the polymer, e.g., the co-monomer is provided in the same inner volume which holds the monomer; the catalyst is an initiator and/or an accelerator, which may be provided in a third inner volume separated from one of the other two inner volumes by a second burstable seal; and the apparatus includes a liquid buffer.

In other preferred embodiments, the apparatus has a tapered nozzle adapted to allow polymer formed in the apparatus to be removed in a controlled fashion from the apparatus; the apparatus is formed as a flexible plastic bag; the outer portion of the flexible plastic bag includes a light absorbing material, e.g., a brown pigment or para amino butyric acid, adapted to prevent photodegradation of chemicals held within the apparatus, or the apparatus is stored in an opaque plastic or cardboard container to prevent such photodegradation; and the inner volumes have little or no oxygen in their gaseous phases to prevent oxidation of chemical components within the apparatus. If riboflavin, or its equivalent, is used as a catalyst some oxygen is provided in the compartment containing the riboflavin to enhance catalysis.

In the most preferred embodiments, the monomer is acrylamide (provided in powdered form); the accelerator is TEMED or DMAPN; the co-monomer is chosen from BIS, BAC, DHEBA, and DATD; the initiator is APS; the buffer is Tris; and the apparatus further includes SDS.

By "all chemical components" is meant all those chemicals necessary for the electrophoretic gel; i.e., any required monomers and co-monomers and liquid buffers.

In another related aspect, the invention features a method for forming an electrophoretic gel. The method includes the steps of providing an apparatus as described above; breaking the burstable seal within the apparatus; allowing the chemical compounds in the inner volumes to contact each other to form a liquid medium; pouring the resulting liquid medium into a holder for the electrophoretic gel; and allowing the liquid medium to form the electrophoretic gel in the holder.

Other features and advantages of the invention will be apparent from the following description of the preferred embodiments thereof, and from the claims.

DESCRIPTION OF THE PREFERRED EMBODIMENT

The drawing will first briefly be described.

DRAWING

The FIGURE is an apparatus for preparation of a polyacrylamide gel.

STRUCTURE

Referring to the FIGURE apparatus 10 is formed as a flexible plastic container (with a non-burstable seam) having compartments with inner volumes 12, 14, 16, and 18 separated by burstable seals 20, 22, and 24. Monomer and co-monomer required for making a polyacrylamide gel are packaged in powder form in one compartment 12 of the multi-compartment container. Gel components with a long shelf-life in liquid form (e.g., TRIS, SDS and water, pH adjusted) are stored in a separate compartment 14 as a liquid. Other compartments 16 and 18 hold the initiator (e.g., APS in powdered form) and accelerator (e.g., TEMED in liquid form) respectively. The individual compartments are kept completely separate from one another by virtue of water and air-tight, yet burstable seams created during the manufacturing process. Although the FIGURE shows four compartments (as would be used for an SDS-PAGE gel, see Example 1), additional burstable seams can be introduced into the package to create additional compartments depending on the specific application.

In order to start the polymerization reaction, the user (wearing gloves and eye protection) needs merely to apply pressure to the package such that the burstable-seams separating the compartments are ruptured. Note that the entire package is surrounded by a heavy duty seam which can not be ruptured by nominal pressures. Once all burstable seams are ruptured, the contents are mixed by gently rocking of the apparatus. One end 26 of the package is shaped into a nozzle so that pouring of the gel is simplified. Once components are mixed, the user simply cuts the end of the nozzle at point 28 with a pair of scissors and pours the liquid into the desired gel apparatus. Polymerization time (the time before which the user must pour the mixed components into the gel apparatus) can be adjusted by changing the absolute concentrations and/or ratios of initiator and accelerator.

All chemical components are sealed into the package under an inert gas, such as nitrogen. This prevents oxidation from occurring, thus allowing the apparatus to be stored at room temperature until use; and it eliminates the need to degas components to remove oxygen which would otherwise inhibit polymerization. Note that in some circumstances, e.g., when riboflavin is used as an initiator, trace amounts of oxygen are required to initiate polymerization and can be sealed into the initiator compartment. When riboflavin is used, all seals are burst and the components mixed and then irradiated with ultraviolet light to start polymerization. The outer portion of apparatus 10 is light sensitive (e.g., provided with a brown pigment) to prevent photodegradation of chemicals. The apparatus is also stored in a light-proof container (not shown). The liquid components are sterile filtered to prevent bacterial and fungal growth during storage.

Although a flexible plastic bag is described above, those in the art will recognize that any other non-chemically reactive container with separate, but readily connectable compartments, is suitable for gel preparation using this system.

The following examples will illustrate the utility and flexibility of this system.

EXAMPLE 1

Preparation of Sodium Dodecyl Sulfate-Containing Stacking and Resolving Polyacrylamide (SDS-PAGE) Gels for One-Dimensional Separation of Proteins This type of gel separates proteins on the basis of size. Two gels are actually required, a high percentage acrylamide resolving gel, and a low percentage acrylamide stacking gel of a different pH. Typically, the resolving gel is poured first into a vertically-oriented gel holding apparatus and allowed to polymerize, then the stacking gel is poured on top of the resolving gel and allowed to polymerize.

Specifically, for the high percentage gel, compartment 14 contains 17.93 ml water containing 45.4 g/l TRIS, and 1 g/l SDS, pH 8.8; compartment 12 contains 2.0 g acrylamide and 0.0533 g BIS; compartment 16 contains 0.0097 g APS powder; and compartment 18 contains 10 μl TEMED. For the low percentage gel compartment 14 contains 7.168 ml water containing 15.256 g/l TRIS, and 1 g/l SDS, pH 6.8; compartment 12 contains 0.315 g acrylamide and 0.0084 g BIS; compartment 16 contains 0.0016 g APS powder; and compartment 18 contains 7.5 µl TEMED.

During use all seals 20, 22, and 24 are simultaneously broken and the compartments mixed gently. The liquid is then poured using standard procedures to form a polyacrylamide gel.

EXAMPLE 2

Preparation of a Urea-Containing Polyacrylamide Gel for DNA Sequencing

The above-described apparatus can be provided with one extra compartment containing urea. The components, and their relative quantities, required to form such an acrylamide gel are generally described in Maniatis, "Molecular Cloning", A Laboratory Manual, 2nd ed., Section 13, 1987.

EXAMPLE 3

Preparation of a Gradient Gel for Protein Separation

Gradient gels for protein separation can be formed using the above-described apparatus using reagents generally as described by Maniatis, supra, Section 18. For the preparation of a gradient gel, two separate apparatuses are provided, each adapted to form an appropriate percentage acrylamide solution. These solutions are then placed into a standard gradient-forming apparatus and a gradient gel formed by standard procedure.

EXAMPLE 4

Non-acrylamide Matrices

Non-acrylamide matrices have been described in the art. For example, AT Biochem, Inc. describes a hydrolink non-acrylamide low molecular weight DNA gel. The above-described apparatus can be adapted to separate the individual components required to form the hydrolink gel in a manner similar to that described for the polyacrylamide gels.

Other embodiments are within the following claims.

I claim:

1. Apparatus for forming an electrophoretic gel comprising a polymer, said apparatus comprising:
at least two sealed compartments, one said sealed compartment having a first inner volume, a second said sealed compartment having a second inner volume, said first and second inner volumes being separated from each other by at least one burstable seal, one said inner volume comprising a monomer which can be polymerized to form said polymer, the other said inner volume comprising a catalyst, wherein bursting of said burstable seal allows said monomer and said catalyst to contact each other and, in conjunction with any other necessary components held within said apparatus, to form a liquid medium in said apparatus, said liquid medium being adapted to form the electrophoretic gel.

2. Apparatus for forming an electrophoretic gel comprising a polymer, said apparatus comprising:
at least two sealed compartments, one said compartment having a first inner volume and the second said compartment having a second inner volume, said apparatus comprising all chemical components necessary to form said electrophoretic gel, wherein one or more of said chemical components is provided in said first inner volume, and one or more of said chemical components is provided in said second inner volume, and wherein said first and second inner volumes are separated from each other by at least one burstable seal, wherein bursting of said burstable seal allows contact of said first and second inner volumes and thereby contact of said chemical components held within said volumes, wherein when all said chemical components are contacted within said apparatus a liquid medium for forming the electrophoretic gel is provided.

3. An apparatus for forming an electrophoretic gel comprising a polymer, said apparatus comprising:
at least four sealed compartments, each said sealed compartment having an inner volume, each said inner volume being separated from other said inner volumes by one or more burstable seals, a first said inner volume comprising a monomer which can be polymerized to form said polymer, a second said inner volume comprising an initiator, a third said inner volume comprising an accelerator, and a fourth said inner volume comprising an aqueous buffer, wherein bursting of said burstable seals allows said monomer, initiator, accelerator, and buffer to contact each other and to form a liquid medium in said apparatus, said liquid medium being adapted to form the electrophoretic gel.

4. The apparatus of claim 3 wherein said initiator is provided in solid form.

5. The apparatus of claim 3 wherein said accelerator is provided in liquid form.

6. The apparatus of claim 1 or 3 comprising a co-monomer which co-polymerizes with said monomer to form said polymer.

7. The apparatus of claim 6, wherein said co-monomer is provided in said inner volume comprising said monomer.

8. The apparatus of claim 1, wherein said catalyst is chosen from an accelerator and an initiator.

9. The apparatus of claim 1 or 2, wherein said apparatus comprises an initiator.

10. The apparatus of claim 9, wherein said initiator is provided in a third inner volume, within a third sealed compartment, separated from one of said first and second inner volumes by a second burstable seal.

11. The apparatus of claim 1 or 2, further comprising a liquid buffer.

12. The apparatus of claim 1, 2 or 3, wherein said apparatus comprises a tapered nozzle adapted to allow liquid medium formed in said apparatus to be removed in a controlled fashion from said apparatus.

13. The apparatus of claim 1, 2 or 3, wherein said apparatus is formed as a flexible plastic bag.

14. The apparatus of claim 13, wherein the outer portion of said flexible plastic bag comprises a light absorbing material adapted to prevent photodegradation of chemicals held within said apparatus.

15. The apparatus of claim 1 or 2, wherein said first and second inner volumes comprise no oxygen in any gaseous phase.

16. The apparatus of claim 1 or 3, wherein said monomer is acrylamide.

17. The apparatus of claim 1, wherein said catalyst is an accelerator chosen from N,N,N',N'-tetramethylethylenediamine and 4-dimethylaminoproprionitrile.

18. The apparatus of claim 16, wherein said acrylamide is provided in powdered form.

19. The apparatus of claim 6, wherein said co-monomer is chosen from N,N'-methylenebisacrylamide, N,N-bisacrylylcystamine, N,N'-(1,2-dihydroxyethylene) bisacrylamide, and N,N'-diallyltartardiamide.

20. The apparatus of claim 9, wherein said initiator is ammonium persulfate.

21. The apparatus of claim 11, wherein said buffer comprises Tris(hydroxymethyl)methylamine.

22. The apparatus of claim 1 or 2, further comprising sodium dodecyl sulphate.

23. The apparatus of claim 2, wherein powdered components are provided in said first inner volume, liquid components in said second inner volume and an initiator and accelerator provided in two separate other inner volumes, at least one said other inner volume being separated from one said first or second inner volumes by a third burstable seal.

* * * * *